(12) United States Patent
Laugharn, Jr. et al.

(10) Patent No.: US 6,270,723 B1
(45) Date of Patent: Aug. 7, 2001

(54) RAPID CRYOBARIC STERILIZATION AND VACCINE PREPARATION

(75) Inventors: James A. Laugharn, Jr., Winchester; David W. Bradley, Bedford; Robert A. Hess, Cambridge, all of MA (US)

(73) Assignee: BBI Bioseq, Inc., West Bridgewater, MA (US)

( * ) Notice: Subject to any disclaimer, the term of this patent is extended or adjusted under 35 U.S.C. 154(b) by 0 days.

(21) Appl. No.: 09/165,829

(22) Filed: Oct. 2, 1998

Related U.S. Application Data

(63) Continuation-in-part of application No. 09/097,852, filed on Jun. 15, 1998, now abandoned.

(51) Int. Cl.⁷ .................................. A61L 2/02; C12N 7/04
(52) U.S. Cl. ................................ 422/39; 422/1; 435/236; 436/543
(58) Field of Search .................................. 422/39, 33, 40, 422/1; 435/236; 424/184.1; 206/367; 436/543

(56) References Cited

U.S. PATENT DOCUMENTS

| | | | |
|---|---|---|---|
| 3,445,568 | 5/1969 | Allen | 424/92 |
| 3,579,999 | 5/1971 | Schwartz | 62/56 |
| 3,617,178 | * 11/1971 | Clouston . | |
| 3,677,022 | 7/1972 | Schwartz | 62/56 |
| 4,164,538 | 8/1979 | Young et al. | 422/26 |
| 4,753,345 | * 6/1988 | Goodsir et al. | 206/366 |
| 5,207,983 | * 5/1993 | Liebert et al. | 422/25 |
| 5,217,687 | * 6/1993 | Sewell | 422/21 |
| 5,288,462 | 2/1994 | Carter et al. | 422/39 |
| 5,300,433 | * 4/1994 | Hrinda et al. | 435/238 |
| 5,316,745 | 5/1994 | Ting et al. | 422/295 |
| 5,455,175 | 10/1995 | Wittwer et al. | 435/286.1 |
| 5,478,910 | 12/1995 | Russell et al. | 528/274 |
| 5,512,462 | 4/1996 | Cheng | 435/91.2 |
| 5,582,831 | * 12/1996 | Shinitzky | 424/277.1 |
| 5,686,045 | * 11/1997 | Carter | 422/33 X |
| 5,902,565 | * 5/1999 | Cox et al. | 424/1.29 |
| 6,120,985 | 9/2000 | Laugharn, Jr. et al. | 435/1.3 |

OTHER PUBLICATIONS

SILVA, Jerson L. et al. "Effects of Hydrostatic Pressure on a Membrane–Enveloped Virus: High Immunogenicity of the Pressure–Invactivated Virus," Journal of Virology, p. 2111–2117, Apr. 1992.*

K.R. Brower, "A Method for Measuring the Activation Volumes of Fast Reversible Reactions. The Ferric Thiocyanate Complex," Journal of American Chemical Society 90(20): 5401–5403 (1968).

Clegg et al., A New Technique for Optical Observation of the Kinetics of Chemical Reactions Perturbed by Small Pressure Changes, Biopolymers 14:883–887 (1975).

Hashizume et al., "Kinetic Analysis of Yeast Inactivation by High Pressure Treatment at Low Temperatures," Biosci. Biotech. Biochem. 59(8):1455–1458, (1995).

Hayakawa et al., Oscillatory Compared with Continuous High Pressure Sterilization on *Bacillus Stearothermophilus* Spores, Journal of Food Science 59(1):164–167 (1994).

Ponce et al., "Sensitivity of *Listeria innocua* to High Hydrostatic Pressure . . . Egg," in *High Pressure Research in the Biosciences and Biotechnology,* Heremans (Ed.), Leuven U. Press (Belgium) pp. 299–302, (1997).

Robert B. Macgregor, Jr., "Reversible Inhibition of EcoRI with Elevated Pressure," Biochemical and Biophysical Research Communications 170(2):775–778 (1990).

Michels et al., "Pressure Dependence of Enzyme Catalysis," in Biocatalysis at Extreme Temperatures, American Chemical Society, pp. 108–121 (1992).

Miller et al., "High Pressure–Temperature Bioreactor: Assays of Thermostable Hydrogenase with Fiber Optics," Biotechnology and Bioengineering 34:1015–1021 (1989).

* cited by examiner

*Primary Examiner*—Elizabeth McKane
(74) *Attorney, Agent, or Firm*—Fish & Richardson P.C.

(57) ABSTRACT

The invention is based on the discovery that biological and non-biological materials can be sterilized, decontaminated, or disinfected by repeatedly cycling between relatively high and low pressures. Pressure cycling can be carried out at low, ambient, or elevated temperatures (e.g., from about −20° C. to about 95° C.). New methods based on this discovery can have applications in, for example, the preparation of vaccines, the sterilization of blood plasma or serum, the decontamination of military devices, and the disinfection of medical equipment. The new methods can also be incorporated into production processes or research procedures.

33 Claims, No Drawings

RAPID CRYOBARIC STERILIZATION AND VACCINE PREPARATION

CROSS REFERENCE TO RELATED APPLICATION

This application is a continuation-in-part of U.S. Ser. No. 09/097,852, filed Jun 15, 1998, and now abandoned, which is incorporated herein by reference in its entirety.

BACKGROUND OF THE INVENTION

The invention relates to methods for sterilizing materials and preparing vaccines.

Various methods and devices exist for the sterilization, decontamination, or disinfection of biological and non-biological materials. These methods include thermal destruction (e.g., burning), heat sterilization, irradiation (e.g., ultraviolet or ionizing irradiation), gas sterilization (e.g., using ethylene oxide), photosensitization, membrane sterilization, or the use of chemical disinfectants (formaldehyde, glutaraldehyde, alcohols, mercury compounds, quaternary ammonium compounds, halogenated compounds, solvent/detergent systems, or peroxides).

Heat sterilization (e.g., autoclaving) is often used, for example, for sterilizing medical solutions prior to use in a patient. Heat sterilization typically requires heating a solution to 121° C. for a minimum of 15 minutes under pressure in an autoclave, maintaining the heat and pressure conditions for a period of time sufficient to kill bacteria, fungi, and protists and inactivate viruses in the solution.

Many reusable medical articles and materials are not suitable for disinfection or sterilization in an autoclave. For example, plastic parts on medical devices, hemodialyzers, and fiber optic devices are commonly sterilized by chemical germicide treatment. In general, germicides require several hours of treatment for the inactivation of microorganisms.

To ensure sterility in pharmaceutical production, gas sterilization is often employed. However, gas sterilization (e.g., using ethylene oxide) can be time-consuming, requiring prehumidification, heating, and evacuation of a sample chamber, followed by treatment with high concentrations of the gas for up to 20 hours at a time.

When properly used, traditional disinfectants can inactivate vegetative bacteria, certain fungi, and lipophilic or medium-sized viruses. However, these disinfectants often do not arrest tubercle bacillus, spore-forming bacteria, or non-lipophilic or small-sized viruses.

Another method for lysing cells, and thereby sterilizing a sample is described in Microbiology (Davis et al., Harper & Row, Hagerstown, Md., 1980). This procedure of freezing and thawing the sample is believed to exert its effect through formation of tiny pockets of ice within the cells when a suspension of bacteria is frozen. The ice crystals and the high localized concentrations of salts both cause damage to the bacteria. A single freezing event is generally sufficient to kill only some of the bacteria, but repeated freeze-thaw cycles result in a progressive decrease in viability. Lethality is correlated with slow freezing and rapid thawing.

Traditional freeze-thaw methods are limited in the speed of the freeze-thaw cycle by the time needed to transfer heat to and from the center of the sample to effect phase changes. The equilibrium rate is particularly slow in the case of large volume samples (e.g., about 100 ml or larger). Sterilization efficiency of the traditional methods is limited by the impracticality of performing a large number of freeze-thaw cycles by those methods.

Traditional methods of food preservation include pasteurization, in which a food is held at an elevated temperature for a period of time.

There is presently a need to develop methods for inactivating microbes and viruses from protein preparations while maintaining the integrity and therapeutic value of the proteins. The development of methods for inactivation of non-encapsulated viruses is especially challenging, since the outer coats of such viruses generally include proteins similar to the proteins one wishes to retain.

SUMMARY OF THE INVENTION

The invention is based on the discovery that biological and non-biological materials can be sterilized, decontaminated, or disinfected by repeatedly cycling between relatively high and low pressures. Pressure cycling can be carried out at low, ambient, or elevated temperatures (e.g., from about −40° C. to about 95° C.). New methods based on this discovery can have applications in, for example, the preparation of vaccines, the sterilization of blood plasma or serum, the decontamination of military devices, food and beverage production, and the disinfection of medical equipment. The new methods can also be incorporated into production processes or research procedures.

In general, the invention features a method for sterilizing a material. The method includes the steps of providing a material at an initial pressure (e.g., 1 atm) and temperature (e.g., 25° C., lower temperatures such as 0° C. or lower); increasing the pressure to an elevated pressure insufficient to irreversibly denature proteins (i.e., less than about 50,000 psi), but still high enough to kill at least some (e.g., at least 25%, 50%, 75%, 90%, 95%, 99%, or even substantially all) pathogens that contaminate the material (e.g., in the range of about 5,000 psi to about 50,000 psi, or in the range of about 10,000 psi to about 30,000 psi); and subsequently decreasing the pressure to the initial pressure or thereabouts, to provide a sterilized material.

The material can be chilled to a subzero temperature (e.g., from about −40° C. to about 0° C., especially between about −20° C. and about −5) either before or after the pressure is increased. The temperature can be subsequently increased, either before or after the pressure is decreased.

The pressure can optionally be repeatedly cycled (e.g., 2, 3, 5, 10, or even 100 or more times) between the elevated pressure and the initial pressure. Such cycling can be carried out at the initial temperature, at a low temperature (e.g., subzero temperatures such as between −40° C. and 0° C., or between −20° C. and −5° C.), or while the material is being cooled to a low temperature. In some cases, a sample at low temperature can be in the solid (i.e., frozen) state at the initial pressure, but in the liquid (i.e., molten, or thawed) state at the elevated pressure. In such cases, pressure cycling causes concomitant freeze-thaw cycling. The temporal pattern of pulsation can, optionally, be altered. During each cycle, the pressure is alternately raised and then lowered. The ratio of the time at high pressure to the time at low pressure is termed as the "pulsation pattern ratio." A pulsation pattern ratio greater than 1:1 (e.g., 2:1 or more) can give optimal inactivation of contaminants in most cases, whereas a pulsation ratio less than 1:1 can give greater retention of properly folded, sensitive proteins.

The material being sterilized can be, for example, a biological sample, blood plasma, serum, living tissue, medical or military equipment, a foodstuff, a pharmaceutical preparation, or a vaccine. The material being sterilized can be initially contaminated with, for example, one or more of a bacterium, a virus, a fungus, a protist, a nucleic acid, or a protein.

Any of the new methods described above can also be used to produce vaccines against specific pathogens. For example, a suspension of pathogenic cells can be obtained, sterilized by one of the new methods (e.g., the method that involves pressure cycling, and potentially freeze/thaw cycling, at a subzero temperature), and combined with an adjuvant to produce a vaccine. If there are toxins present in the suspension, these can removed (e.g., after the sterilization step).

The new methods can be carried out in a pressurization vessel. The pressurization vessel can, for example, contain a gas (e.g., air or an inert gas such as nitrogen). The gas can be involved, for example, in a cavitation process. Cavitation is pressurization in the presence of a gas, followed by a rapid depressurization, resulting in the explosion of cells as microscopic gas bubbles form. This method of cell disruption can also be termed explosive decompression.

In some cases, it can be useful to include a phase-change catalyst (e.g., glass particles) in conjunction with the material to be sterilized. The catalyst can subsequently be removed by centrifugation or filtration, if necessary.

Materials sterilized by any of the above methods are also considered to be an aspect of the invention.

In another embodiment, the invention features an apparatus for sterilizing a material. The apparatus includes a pressurization vessel adapted to transmit an external pressure to a material within itself. The vessel needs to be capable of withstanding an elevated pressure (e.g., pressures encountered in the practice of any of the new methods described above), must be capable of fitting in a pressure cycling apparatus (e.g., such as those described in U.S. Ser. No. 96/03232, which was given U.S. Ser. No. 08/793,213 in the U.S. National Phase and issued on Mar. 14, 2000 as U.S. Pat. No. 6,036,923, and may include a valve that allows aseptic recovery of the sterilized material. In some cases, the apparatus can also include heating and cooling devices (e.g., a heater and a refrigerator).

In still another embodiment, the invention features a method for sterilizing a sample that includes proteins. The method includes the step of providing the sample at an initial pressure; rapidly increasing the pressure to a pressure sufficient to inactivate pathogens; and quickly restoring the initial pressure to provide a sterilized sample and to avoid substantial aggregation of proteins.

In yet another embodiment, the invention features another method for sterilizing a sample that includes proteins. The method includes the steps of providing the sample at an initial pressure; adding one or more protein stabilizing reagents (e.g., sugars such as glucose; glycerol; a hydrophilic polymer; a cyclodextrin; a caprylate; acetyl tryptophanoate; polyethylene glycol; an anti-oxidant; or a protein specific ligand) to the sample; increasing the pressure to an enhanced pressure (e.g., about 10,000 to 70,000 psi, depending on the stability of the protein); incubating the sample for a time sufficient for sterilization to occur without substantial loss of protein function; and restoring the pressure to the initial pressure, to provide a sterilized sample.

The invention also features a method for disruption of cells or tissue or inactivation of microbes. The method includes the steps of freezing the sample; and pulsating the pressure while maintaining the sample in the solid phase, to disrupt the cells.

Another embodiment of the invention features a method for inactivating proteins in a sample. The method includes the steps of adding to the sample a reagent containing moieties that can react with amines, thiolates, carboxylates, imidazoles, or other functional groups typically found on proteins (e.g., isothiocyanates, maleamides, succinimides, sulfonyl chlorides), to form a reaction mixture; and pressurizing the reaction mixture, to inactivate the proteins. A protein stabilizing agent can optionally be added (e.g., prior to sterilization).

In any of the above methods, the material to be sterilized can be provided in its final packaging, the packaging being able to transmit pressure without rupture. For example, the packaging can be hermetically sealed in flexible plastic. Alternatively, the packaging can be a syringe and the pressure can be transmitted via a plunger.

The invention also features a method for pressurizing an infectious sample. The method includes the steps of charging the sample into a container adapted to transmit an external pressure to the sample; submerging the container in a sterilizing chemical solution (e.g., containing an oxidizing agent); and pressurizing the sample within the container.

As used herein, the term "subzero temperature" means a temperature lower than 0° C. (e.g., −1° C., −5°, −10° C., −20°, or lower). All temperatures herein are in degrees Celsius unless otherwise stated, and are simply denoted by "° C.". Units of pressure herein are expressed in pounds per square inch (psi) or in atmospheres (atm). 1 atmosphere is about 14.7 psi, 1 bar, or 101.3 kilopascals.

A "cryobaric process" is a process that involves at least one pressure change carried out at a subzero temperature. In some cryobaric processes, the pressure is cycled between two pressures (e.g., about 14.7 psi to about 35,000 psi) while the temperature is either maintained at a subzero temperature or varied within a subzero temperature range.

The terms "sterilize", "disinfect", and "decontaminate" are used interchangeably herein, unless otherwise demanded by the context. It should be noted that "sterilization" (killing of all organisms) may not be synonymous in certain operations with "decontamination" when the contaminant is nonliving, such as a protein or prion.

The new methods provide several advantages. For example, the methods can be carried out at subzero temperatures (e.g., between about −40° C. and 0° C.). Pressure cycling carried out at subzero temperatures can advantageously induce oscillation between different phases of water within or outside the cells or vesicles of biological contaminants. The transition between the liquid and solid states can create physical stress on membranes, walls, and vesicles, thereby facilitating the intended processes. The range of subzero temperatures generally used in the new methods is easily accessed with relatively inexpensive equipment (e.g., commercial freezer devices) that is readily available in a range of shapes and sizes to fit a specific need. Similarly, the range of pressures required for the standard operation of the methods (e.g., from about 14.7 psi to about 30,000 psi) can be generated by devices as described in U.S. Ser. No. 96/03232, which was given U.S. Ser. No. 08/793,213 in the U.S. National Phase and issued on Mar. 14, 2000 as U.S. Pat. No. 6,036,923.

An apparatus for sterilization of a material by a cryobaric process will generally include a chamber for containing the material, the chamber being capable of operation at a selected elevated pressure: and a system for controlling, altering, or regulating the temperature and pressure within the chamber. The apparatus will also provide systems for removing a sterilized material in an aseptic manner from the chamber. Additionally, a typical sterilization apparatus for use with the new methods can include a variety of controls, regulators, and temperature, or pressure sensors. The pressurizing medium can be, for example, a water/ethylene glycol solution or other non-freezing solution or a solid such as powdered talc.

Variation of temperature can aid lysis of microbes and contaminating biological materials. Different types of cell membranes, walls, or vesicles can necessitate different conditions of temperature, pressure, cycle count, or cycle frequency to maximize the effectiveness of the sterilization processes.

The devices necessary for carrying out the new methods can be easily adapted to conform the requirements of particular applications. For example, a small, portable device can be obtained, thereby allowing sterilization or decontamination procedures to be carried out in the field (e.g., by paramedics or military medical personnel).

The new methods are very rapid. For example, the pressure can be cycled at a frequency of about 1 mHz to about 10 Hz, allowing the entire sterilization process to be completed within five minutes or less. Heat generated by cycling frequencies greater than 10 Hz can be destructive to fragile proteins. Nonetheless, frequencies higher than 10 Hz can also be used, when the heat generated by the cycling process would not be expected to be deleterious to the specific sample, or adequate measures are taken to remove heat.

The new methods allow pathogenic organisms in a sample to be neutralized without concomitant denaturation of proteins. The new methods can avoid denaturation, which often occurs upon sterilization of biological samples.

Rapid and economical sterilization is achievable with a minimum of protein destruction or denaturation. The new methods can thus be advantageously used for the production of highly active vaccines. These vaccines can be superior to vaccines produced at higher temperatures, since high temperatures can cause disruption of both covalent and noncovalent bonds in proteins, and can lead to a greater degree of irreversible denaturation than the methods claimed here.

Other advantages of the new methods include the avoidance or reduction of the need for addition of chemical additives to blood fractions; scalability of the process from single units to large, pooled samples or to continuous, on-line processes; and elimination of side effects of thermal inactivation processes on protein components.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides a method by which a material can be sterilized or decontaminated by high pressure in the range of about 5,000 to 50,000 psi, preferably in the range of 10,000 to 35,000 psi. The material is adjusted, either before or after pressurization, to a particular temperature which is both compatible with preserving the desirable properties of the material, and which also allows destruction of the contaminants.

Although the temperature, pressure, number and duration of cycles, and relative timing of pressure and temperature changes can vary, the new methods are in general carried out according to the following procedure: A material is provided at initial pressure (e.g., atmospheric pressure, 14.7 psi) and temperature (e.g. ambient temperature, 25° C., or a refrigerated temperature such as 0° C. to 4° C., or a frozen temperature such as −80° C. to −20° C.). The material is then pressurized to an elevated pressure. The temperature can optionally be decreased (e.g., to a subzero temperature such as −40° C. to 0° C., preferably from about −20° C. to about −5° C.). The pressure can then be cycled repeatedly between the elevated pressure and ambient pressure. The sample can be produced in a frozen state after the final depressurization, or can be warmed to 0° C. or higher before depressurization to produce a non-frozen, sterilized product.

Other operational steps can be combined with these unit operations. For example, although a sample can be suspended or dissolved in a solvent or solution and the suspension or solution can be pressurized directly, induction of cavitation in a liquid material can be useful (e.g., for sterilizing tissue samples). In this process, the sample is pressurized along with a gaseous headspace followed by rapid release of pressure. This process can produce microscopic gas bubbles in the sample.

For most applications, an air headspace would suffice for cavitation. If fragile proteins are to be isolated, however, it may be preferable to use an inert gas such as nitrogen. Again, pulsing can be carried out at a frequency of about 1 mHz to about 10 Hz. More rapid pulsing (e.g., in the ultrasonic range) can be used if the heat generated does not damage critical components such as proteins in the sample.

The extent of cavitation necessary for sterilization depends on the type of biological contaminant and the goal of the sterilization process. For example, microbes that include a cell wall (e.g., yeast) can require more rigorous cavitation. If sterilization is intended to destroy microbial cells without significantly decreasing the biological activity of the macromolecules (e.g., proteins; nucleic acids) within those cells, then it can be preferable to use an inert gas for cavitation. The ratio of liquid to gas in most cavitation methods used with the new sterilization methods will be about 1:1 to about 1:10, although ratios outside of this range may also be used. The process differs from known sterilization methods in that either much higher pressures or else cycles of high and low pressures are used. Diffusion of gases is more rapid, and microbe destruction is greater.

The above processes can also be used in conjunction with methods in which a known static pressure and/or a particular pressure is maintained for a given time. In some cases, the pressure may be maintained at a greatly elevated level for an amount of time sufficient for microbe inactivation but insufficient for irreversible protein denaturation.

If a phase change is involved in any sterilization process, a catalyst may be added to accelerate the change. For example, finely-divided glass or other materials can serve as nucleation sites for freezing of a sample or material, or as a site for inducing nucleation of bubbles.

General

Although nearly any biological or non-biological material can be sterilized, decontaminated, or disinfected by the new methods, biological materials containing fragile proteins in relatively low quantities (e.g., ng, pg, or even fg range) or high concentrations can present a special problem, especially if the integrity of the proteins is to be maintained throughout the sterilization process.

Applications of the new methods include the sterilization of blood plasma from donors (e.g., for use in transfusions), sterilization of water, sterilization of foodstuffs (e.g., jams, jellies, meat-, fruit-, or vegetable-derived products, fruit juice, apple cider, milk), decontamination of medical equipment (e.g., surgical and dental instruments such as scalpels, blades, and drills), neutralizing medical samples (blood, urine, fecal, hair, biopsy, or other tissue samples) or military equipment (e.g., instrumentation and integrated circuits) to destroy infectious agents, production of pharmaceuticals (e.g., generation of antisense drugs from biological sources), and disinfection of dry goods (e.g., clothing, bedding, and linens). The new methods can be used to arrest the growth of incubated materials or to sterilize such materials. The new methods can also be used to ensure sterility of cosmetics, pharmaceutics, and industrial products.

Examples of microbes that can be inactivated by the new methods include both hydrophilic and lipophilic viruses; nearly any bacteria, including, for example, Staphylococci, Micrococci, *Pyogenic streptococci*, diphtheroids (e.g., lipophilic, non-lipophilic, anaerobic diphtheroids such as Propiobacterium), gram-negative enteric bacilli (e.g., Escherichia, Enterobacter, Klebsiella, Proteus, Serratia), Neisseria, aerobic spore formers, mycobacteria; fungi, including, for example, yeast, *Pityrosporum ovale, Pityrosporum orbiculare, Candida albicans, Candida parapsilosis, Torulopsis glabarata*, and *filamentous dermatophytic* species; protists and lower multicellular organisms, including protozoan parasites; and helminth parasites; malaria-inducing organisms; and giardia.

Plasma pools often contain hepatitis C virus (HCV). Procedures for producing blood products can thus benefit from a process that inactivates HCV and other viruses. Human parvovirus B19 (B19), is another common contaminant of plasma. Hepatitis A virus (HAV) contaminants are less common, but still troublesome. Both B19 and HAV are small (about 15–30 nm), do not possess an outer envelope composed of lipids (non-enveloped), are resistant to heat and chemical treatment, and are difficult to remove by nanofiltration. Enveloped viruses (e.g., HIV, HBV, HCV) are also potential targets of the new methods. Currently uncharacterized viruses, such as some newly-recognized forms of hepatitis virus and transfusion transmitted virus (TTV) can also be vulnerable to the new methods. In addition, prion-based infectious agents such as transmissible spongiform encephalopathies are difficult to screen and to inactivate. However, because the methods of the invention can, under suitable conditions, induce protein unfolding, it may be possible to inactivate such agents by the methods of the invention.

Due to the possibility that disrupted virus particles can re-assemble after pressure treatment, it can be desirable to irreversibly degrade the nucleic acids contained in the virus. Moderately high pressures (e.g. 20,000 psi to 60,000 psi) can disrupt complexes of nucleases and their endogenous inhibitors. Additionally, moderate pressure can accelerate the activity of uninhibited enzymes. The process may be enhanced by the addition of nucleases. It is desirable in some cases to add a magnesium independent nuclease, as in the treatment of citrated plasma.

Alternatively, much higher pressures (e.g. 50,000 psi to 150,000 psi) can be used for sterilization of materials that are pressure-stable, such as small molecule pharmaceuticals or thermostable proteins. A pressure cycling freeze-thaw sterilization method (e.g., a method that takes advantage of the cyclic formation of high pressure ice such as ice III, ice IV, ice V or ice VI) may also be used.

When the biological contaminants are relatively pressure stable and the sample contains labile proteins that need to be retained, a variation of this method can be used. In this variation, the pressure is increased rapidly (e.g., in less than 5 seconds, or less than 1 second) to a very high maximum pressure (e.g., 150,000 psi), and held at high pressure only briefly (e.g., less than 5 seconds). The pressure is then rapidly released (e.g., in less than 5 seconds, or less than 1 second). The inactivation of pathogens such as viruses can proceed at a much greater rate than the irreversible aggregation of protein molecules, especially at conditions of high pressure and low temperature that increase the solution's viscosity. Under certain conditions of high pressure and low temperature (e.g., 110,000 psi and $-10°$ C.), high pressure ice (i.e. ice V or ice VI) can form. Proteins that are trapped in the lattice structure of the high pressure ice are less likely to aggregate. The high pressure ice takes a finite amount of time to melt, this time being sufficient for the proteins in the sample to refold while trapped in the solid phase.

Pressure has also been shown to increase the activity of numerous enzymes. For example, RNase activity is accelerated by elevation of hydrostatic pressure. This effect can be exploited in conjunction with the new methods for the inactivation of viruses. RNA viruses are readily degraded following high pressure treatment.

Blood Transfusion

The new methods can be used to improve the safety of blood transfusions. Plasma protein products are needed, for example, by hemophiliacs, cancer patients, and kidney dialysis patients. However, viruses and other pathogens frequently present in blood products can present a risk for patients in need of those products. Even using new filtration techniques that eliminate many cells, certain bacteria and viruses can remain in the products.

Ordinarily, blood plasma is isolated by obtaining a blood sample, centrifuging the sample in a plasma separation tube, and decanting the plasma from the precipitate in the tube. Although this method frees the plasma from the bulk of the cells, some cells inevitably remain in the plasma. If the remaining cells include, for example, bacteria or viruses, diseases can be spread by transfusion. The new methods can be carried out on the plasma obtained from the above decanting method. The contaminants that remain in the plasma can be inactivated by the new methods.

Sterilization of Reagents and Media

The new methods can also be used to sterilize industrial products. For example, bovine serum is often used in molecular biology laboratories for cell cultures. Microbial contamination of the source stock material from the supplier occurs infrequently; when it does happen, however, the economic costs and time delays can often be significant. Current methods for sterilization of fetal calf serum (e.g., heat or filtration) can inactivate functionally important proteins (e.g., growth hormones) and also cause variability from lot to lot. Moreover, even if the source stock material is initially sterile, it can become inadvertently contaminated upon opening in the laboratory. The new methods can be used in either a production process (e.g., batch or continuous) or used in individual laboratories for pretreatment of serum or other media prior to initiation of an experiment.

Vaccine Production

The techniques of low-temperature pressure perturbation and ultra-high pressure cavitation described above can be used advantageously in the production of vaccines. Vaccines are typically prepared by subjecting a solution of cultured pathogens to an inactivating treatment (e.g., heating, or addition and removal of chemical denaturants).

A successful vaccine preparation method should ideally result in a high degree of pathogen inactivation, but should allow the solution of pathogen to retain its ability to stimulate a protective immune response in the patient. Cryobaric procedures are well suited to meet the criteria needed for successful vaccine production: since cold, pressure-denatured proteins retain a more native-like structure than do heated or chemically-denatured proteins, pressure inactivated pathogens can thus be more immunogenic. Pressure-denatured proteins are also less likely to aggregate, thereby providing higher yields of vaccine. The pressure-inactivation methods described herein can be economical on a large scale since there are generally no chemicals to add or remove and, unlike heat, pressure can be transmitted rapidly through a large sample.

In general, vaccine production by the new methods involves pulsation of pressure at sub-zero temperatures and/or ultra-high pressure cavitation treatments as described above. The specific conditions necessary for vaccine production can vary depending on the particular pathogen to be inactivated. For example, in the case of spore forming organisms, an optional pretreatment with low pressure and moderate temperature (e.g. 10000 psi and 40° C.) can be applied to cause the spores to germinate. The germinated spores can then be inactivated by the methods of the invention.

Pressure Enhanced Photosensitization of Nucleic Acids:

A method of sterilization has been described, wherein the product to be sterilized is mixed with a chemical agent that can preferentially bind to DNA or RNA and react with the nucleic acid (Radosevich, "Seminars in Thrombosis and Hemostasis," Vol. 24, No. 2, pp. 157–161, 1998). In some cases, light is used to activate the chemical moiety. Disadvantages of such a method can include collateral damage to the desired molecular components of the product to be sterilized (e.g., via non-specific reaction with chemicals or irradiation, or by imperfect or slow penetration of the inactivating chemical to the interior of the pathogen). The application of elevated pressures can substantially overcome these problems by permeabilizing cells and viruses to allow entry of the inactivating chemicals. Elevated pressures can also enhance the affinity and selectivity of the molecules for the nucleic acids, thereby allowing the use of lower chemical concentrations or lower amounts of irradiation. Thus, a faster, less expensive, and more efficient method is obtained.

An apparatus for the execution of the photochemical method can include a high pressure flow-through system such as described in PCT Appln. U.S. Ser. No. 96/03232, which was given U.S. Ser. No. 08/793,213 in the U.S. National Phase and issued on Mar. 14, 2000 as U.S. Pat. No. 6,036,923, having a reaction chamber that includes at least one pressure-resistant window which can be made of a material such as quartz or sapphire, and a device for irradiation of the sample through that window. The flow of liquid is such that all of the sample passes through the irradiated area. The sample can then be collected aseptically. The sample can be introduced into the reaction chamber at high pressure or at low pressure, and then pressurized prior to irradiating.

Pressure-Shock Sterilization

In another embodiment of the invention, the sample is subjected to an elevated pressure for a brief time. The pressure and time are chosen to provide a high degree of pathogen inactivation, but the time is brief enough that proteins denatured by the elevated pressure conditions do not have time to aggregate into irreversible complexes to a sufficient extent before the refold into heir native forms. The method can be enhanced by conditions that slow the rate of aggregation and increase the rate of protein refolding. For example, low temperatures or very high pressures can slow the rate of protein aggregation, and the addition of glucose can increase the rate of protein folding.

Chemical Inactivation of Viruses

A variety of chemicals (e.g. iodine, ethyleneimine, ascorbic acid, thiophosphamide, congo red, paraformaldehyde) can be used to sterilize solutions containing labile proteins. Use of such chemicals can have negative effects, however, including slow inactivation, potential for protein damage, or the inability of compounds to penetrate to the interior of the pathogen. Elevated pressure can enhance the sterilization activity of these chemicals without exacerbating the negative effects.

Stabilization of Proteins and Enzymes

In some cases, it may be desirable to sterilize a solution or other sample containing an unstable protein that would be irreversibly denatured at the pressure necessary for the sterilization procedures described above. In these cases, a stabilizing agent (e.g., amino acids such as amino acids, such as glycine, or specific ligands of proteins in the mixture, ligands of proteins to be recovered, or sugars such as glycerol, xylose, or glucose) can be added to the sample prior to pressurization. For example, caprylate and acetyl tryptophanoate can be added to blood plasma samples, and the plasma samples can then be subjected to the cryobaric sterilization process without excessive destabilization of specific plasma proteins. The stabilizer can then be removed by standard methods (e.g. dialysis, filtration, chromatography).

Pressure Treatment of Infectious Samples

Hydrostatic or pulsating pressure can be a useful tool for sterilization, cell and virus disruption, and nuclease inactivation for samples that may potentially contain agents of infectious disease. Moreover, general safety considerations call for the prevention of infection of the persons handling the sample and the avoidance of contamination of other samples. One way to prevent such contamination is to use a sterilizing solution (e.g., 10% Clorox™ bleach) or other oxidizing agent as a pressurizing medium.

For example, the sample can be placed inside an enclosed and flexible container, which can then be immersed in the chemical sterilizing solution. The solution can then be sealed inside of a second, chemically inert container (i.e., to keep it from contacting the metal parts on the inside of a pressurization chamber). An inert pressurizing medium can then be used to fill the volume between the inside of pressurization chamber and the container holding the sample and sterilizing solution. The container that holds the sterilizing solution can be, for example, a plastic bag, a screw top plastic container, a capped syringe, or a shrink wrapping.

The invention will be further described in the following examples, which do not limit the scope of the invention described in the claims.

EXAMPLES

Example 1

Pressure-cycling Inactivation of *Escherichia coli*-Inoculated Serum

A culture of ampicillin resistant *E. coli* strain in LB/amp media (Luria broth containing 50 μg/ml ampicillin) was grown to saturation. A sample of adult bovine serum (Sigma) was inoculated with 30 μl *E. coli* solution per ml serum. Aliquots (280 μl each) of the inoculated serum were placed into nine micro-centrifuge tubes. The samples in the nine tubes were subjected to the following experimental conditions:

Sample 1 was left untreated as a control.

Sample 2 was maintained at atmospheric pressure (i.e, about 14.7 psi) as the temperature was cycled twenty times between about −17° C. and ambient temperature (i.e., about 25° C.) over 20 minutes.

Samples 3–6 were cooled to −15° C. at atmospheric pressure. The samples sat for 2 minutes to ensure thermal equilibrium. The samples were then subjected to pressure cycles at a rate of about 30 sec/cycle, or 2 Hz. Sample 3 was cycled ten times between about 14.7 psi and about 15,000 psi over 5 minutes; sample 4 was cycled ten times between about 14.7 psi and about 35,000 psi over 5 minutes; Samples 5 and 6 were cycled twenty times between about 14.7 and about 35,000 psi over 10 minutes.

Sample 7 was cycled twenty times between about 14.7 psi and about 35,000 psi at ambient temperature over 6 minutes, forty seconds.

Samples 8 and 9 were subjected to static pressurization for 2.5 minutes; sample 8 was pressurized at ambient temperature and sample 9 was pressurized at −15° C.

Dilutions of the samples were made in LB/amp media, and the samples were plated. Colony forming units per milliliter (CFU/ml) are shown below, along with log reductions (i.e., relative to the control):

| Sample # | CFU/ml | Log reduction |
| --- | --- | --- |
| 1 | $1 \times 10^6$ | 0 (control) |
| 2 | $3 \times 10^5$ | 0.5 |
| 3 | $<1 \times 10^6$ | >0 |
| 4 | $8 \times 10^4$ | 1.1 |
| 5 | $1 \times 10^4$ | 2.0 |
| 6 | $6.4 \times 10^4$ | 1.2 |
| 7 | 80 | 4.1 |
| 8 | $9.6 \times 10^3$ | 2.0 |
| 9 | $4 \times 10^4$ | 1.4 |

Thus, the most effective treatment was that corresponding to sample #7, cycling to 35,000 psi at about 25° C. The results indicate that cycling was more effective than static pressurization at the same temperature (cf. sample #8).

Example 2
Cryobaric Deactivation of Lambda Phage

For each of 4 samples, 2.5 µl Lambda phage stock ($5 \times 10^{11}$ pfu/ml) was diluted 100-fold by addition of about 248 µl calf serum. A fifth 2.5 µl lambda phage stock sample was diluted 100 fold in suspension medium. Two phage-serum samples (250 µl) were frozen by immersing tubes in an ethanol-dry ice bath; three other samples were placed on ice.

One of the frozen phage-serum samples was cycled between 36,000 psi (30 seconds) and 14.7 psi (30 seconds) for 5 minutes. During pressure treatment, the temperature of this sample was maintained at −10° C. The remaining frozen sample was left at 14.7 psi throughout the experiment as a control. When this experiment was repeated, a dry-ice sample was warmed to −10° C. for 5 minutes. A third phage-serum sample was pressurized to 36,000 psi for 10 minutes at 23° C. The two remaining samples, used as positive controls, were a phage-serum sample incubated at 23° C. for 10 minutes with no pressure treatment and a phage-Suspension medium (i.e., 0.0496 M sodium chloride, 4.06 mM Magnesium sulfate, 50 mM Tris-Cl pH 7.5, and 1.0 g/l gelatin) sample with neither pressure nor temperature treatment, respectively. After pressure treatment, $10^2$, $10^4$, and $10^6$ fold dilutions of phage samples were made in Suspension medium.

A culture of ampicillin resistant *E. coli* was grown to saturation in Lambda Broth (i.e., 10 g/l tryptone, 0.042 M sodium chloride), 0.2% maltose, and 10 mM magnesium sulfate (Current Protocols in Molecular Biology, page 1.11.1).

To induce infection, 100 µl of the phage sample was added to 300 µl of the *E. coli* culture prepared above, and the culture was incubated for 10 minutes at 37° C. 2.5 ml Lambda Top Agar (i.e., 10.0 g/l tryptone, 42 mM sodium chloride, 7 g/l agar) was added to each phage-*E. coli* mixture, vortexed, and immediately spread onto Lambda plates (i.e., 10 g/l tryptone, 0.042 M sodium chloride, 10.0 g/l agar in 90 mm petri dishes).

After incubation of the plates for 16 hours at 37° C., lambda plaques were either counted, or, for plates with high confluence, the total surface area covered by plaques was estimated. The plaque forming units (pfu) were calculated by multiplying the dilution factor by the number of plaques appearing on each plate.

The plaque forming activity of Lambda phage was reduced by 5 orders of magnitude by alternating hydrostatic pressure at −10° C. The density of the frozen, pressure-cycled sample was found to be $9.4 \times 10^5$ pfu/ml, while that of the frozen, unpressurized control was $3.2 \times 10^{11}$ pfu/ml. In a second experiment, the plaque forming activity was reduced from $9 \times 10^{10}$ pfu/ml to $6.4 \times 10^4$ pfu/ml after alternating pressure treatment. In contrast to the frozen samples, there was only a 3-fold decrease in plaque forming activity in the room temperature samples. The sample held at 36,000 psi for 5 minutes at 23° C. yielded $1.2 \times 10^{11}$ pfu, and the control maintained at 14.7 psi had $3.1 \times 10^{11}$ pfu.

Serum had very little if any effect on plaque forming activity. There were $50 \times 10^{11}$ pfu in the sample diluted in Suspension medium, and the sample diluted 100-fold into serum decreased only to $3.1 \times 10^{11}$ pfu. Freezing just once at atmospheric pressure (14.7 psi) apparently had no effect on plaque forming activity. There were $3.2 \times 10^{11}$ pfu in the frozen sample and $3.1 \times 10^{11}$ pfu in the sample incubated at room temperature (23° C.).

Example 3
Effect of Pulsation Frequency of Viral Inactivation.

An experiment was carried out to determine the effect of pulsation frequency on the inactivation of lambda bacteriophage in serum.

A serum sample was inoculated with the virus and treated as in Example 2, but with varying frequencies of pulsation and a maximum pressure of 40,000 psi. All samples were treated at −6° C., the total time of treatment for all samples was 15 minutes, and the time spent at high and low pressures was 7.5 minutes in each experiment. The experiment was carried out twice for each set of experimental conditions. The viral titers were measured as in Example 2.

A parallel experiment was carried out on a model of a therapeutic protein to see if its activity was maintained. Anti fluorescein goat IgG (Chemicon International; Tecuma, Calif.) was prepared to a concentration of 4 mg/ml in 5% glucose and 0.3% NaCl. The solution was then subjected to the same treatment as in the bacteriophage inactivation experiment and assayed by measurement of the ability to quench the fluorescence of a 50 nM solution of fluorescein.

The following data were obtained:

| Frequency (cycles per hour) | phage titer (trial #1) | Trial #2 | % IgG activity |
|---|---|---|---|
| 0 | $5.0 \times 10^8$ | $1.1 \times 10^7$ | 100 |
| 4 | $4.6 \times 10^4$ | $9.9 \times 10^2$ | 94 |
| 12 | $3.0 \times 10^3$ | $7.7 \times 10^2$ | 97 |
| 20 | $3.4 \times 10^2$ | $5.0 \times 10^1$ | 92 |
| 40 | $4.8 \times 10^2$ | 0 | 95 |
| 60 | $7.0 \times 10^1$ | 0 | 100 |

This experiment demonstrates that the pulsation of pressure at low temperature can have a significant effect on the rate of viral inactivation, and can be useful in the production of therapeutic blood products. The process can operate under conditions of pressure and temperature that are consistent with high recovery of properly folded therapeutic proteins and can be effective against many types of viruses.

Example 4

Acceleration of Nuclease Activity in a Hyperbaric Sterilization Process

Adult bovine serum is diluted to 50% (v/v) with water and chilled to 0° C. Four aliquots of the serum are dispensed into 250 μl microcentrifuge tubes such that there is 25 μl of air in each tube. The tubes are kept on ice until use. 2 μg of pUC19 plasmid DNA and 2 μg of yeast total RNA (Sigma) in 5 μl of 50 mM Tris buffer, pH 8.0, are added to each sample at the appropriate time. 5 μl of water is added to sample #4 before pressurization. The reactions are stopped by adding of 10 mM vanadyl ribonucleoside complexes and placing the samples on ice. The treatment of these samples are as follows:

Sample #1: control sample (i.e., nucleic acids only). In this sample, the vanadylribonucleosides are added prior to the nucleic acids.

Sample #2: serum and nucleic acid mixture, incubated at 25° C. for 10 minutes. The reaction is immediately stopped as described above.

Sample #3: serum and nucleic acid mixture, pressurized to 60,000 psi at 25° C. for 10 minutes. The reaction is stopped as described above.

Sample #4: serum, pressurized to 60,000 psi at 25° C. for 10 minutes; the nucleic acids are then added, the mixture is incubated for 10 minutes, and the reaction is stopped as described above.

All samples are extracted with an equal volume of phenol/chloroform/isoamyl alcohol mixture to remove proteins, followed by precipitation of the nucleic acids in 70% ethanol. The nucleic acid pellet is re-dissolved in 20 μl of TE buffer. 10 μl of the resulting solution is loaded on a 0.8% agarose gel for electrophoresis. After electrophoresis, DNA is visualized by ethidium bromide fluorescence. 5 μl of the remaining sample is quantified using PicoGreen and Ribogreen dyes (Molecular Probes).

Samples #3 and #4 both show increased degradation with respect to sample #2. The nucleic acids in sample #4 are more degraded than the nucleic acids in sample #3. These results demonstrate that pressure can accelerate blood nucleases both by directly stimulating activity and by releasing inhibitors.

Example 5

Pressure- and Temperature-Induced Inactivation of *Saccharomyces cerevisiae*

*Saccharomyces cerevisiae* was grown in YPD liquid medium (1% yeast extract, 2% peptone, 2% dextrose) until the cultures reached a density of $2 \times 10^6$ cells/ml. The *S. cerevisiae* samples were then diluted 1:10 in calf serum and then subjected to various pressures and temperatures.

First, the temperature was held constant at 23.8° C. during a pressurization process. One sample was maintained at 36,000 psi for 10 minutes at 23.8° C. A second sample was cycled between 36,000 psi and 14.7 psi at 30 second intervals for 10 minutes at 23.80° C. The pressure and temperature were held constant at 14.7 psi and 23.8° C., respectively, for a third sample as a positive control.

For the next three samples, temperature was reduced while equivalent pressure treatments were carried out. Thus, a fourth sample was cooled to −3.6° C. and then pressurized to 36,000 psi for 10 minutes. A fifth sample was also cooled to −3.6° C., then subjected to 10 cycles of pressure alternating between 36,000 psi and 14.7 psi at 30 sec intervals. As a positive control, a sixth sample was cooled to −3.6° C., but was not subjected to pressure treatment.

After the requisite pressure and temperature treatments, all of the samples were diluted by factors of 10, 100, and 1000, spread on LPD plates (1% yeast extract, 2% peptone, 2% dextrose, 1.5% agar), and grown at 32° C. for 24 hours. The number of colony forming units (cfu) were calculated by multiplying the number of colonies by the dilution factor.

A pronounced inactivation of *Saccharomyces cerevisiae* by pressure treatments was observed at both 23.8° C. and −3.6° C. The colony forming activity of the pressurized sample ranged from $1 \times 10^2$ cfu to $5.6 \times 10^3$ cfu for the pressurized samples. The positive controls ranged in colony forming activity from $1.1 \times 10^5$ cfu to $9.2 \times 10^5$ cfu. Thus, the colony forming ability of *Saccharomyces cerevisiae* was decreased by approximately 2 to 3 orders of magnitude.

Example 6

Pressure and Temperature Induced Inactivation of the Moloney Murine Leukemia Virus A retroviral vector, pLNCX, containing Phi+ (the extended viral packaging signal) and a neomycin resistance marker (Neor), but lacking viral structural genes, was used in conjunction with a packaging cell line, NIH-Cyt2. The NIH-Cyt2 cells express the gag, pol, and env viral structural genes necessary for particle formation and replication, but not the RNA packaging signal Phi+. Thus, the pLNCX vector and NIH-Cyt2 cell line together produce infectious, replication-incompetent particles structurally identical to the Moloney Murine Leukemia Virus (MMLV). These infectious MMLV particles contain RNA encoding the pLNCX vector.

MMLV infectious particles, suspended in DMEM with 10% calf serum (CS), are maintained at 4° C. and 14.7 psi except during the pressure and temperature treatments described below. Hydrostatic pressure for one sample is cycled between 35,000 psi and 14.7 psi at 30 second intervals while the temperature is maintained at 2° C. As a positive control, the temperature of a second sample is maintained at 2° C. for 10 minutes at 14.7 psi. A third sample is cycled between 35,000 psi and 14.7 psi at 30 second intervals at −10° C. A fourth sample is held at 35,000 psi for 5 minutes at −10° C. As a positive control, a fifth sample is frozen in dry ice and then warmed to −10° C. for 5 minutes.

Samples are added to dishes of NIH-Cyt2 cells and incubated at 37° C. for 30 minutes to transfect cells with the retroviral vector pLNCX. As a negative control, one plate of cells is mock-transfected with viral-free DMEM-CS. The cells are grown in DMEM with 10% calf serum and G418 which only allows cells with Neor to grow and thus selects for stable transformants. After a 10 day period, the dishes are rinsed with PBS, stained with methylene blue, rinsed again with PBS, and then the colonies are counted. The viral titer, expressed in colony forming units (cfu), is calculated by multiplying the dilution factor by the number of colonies.

Example 7
Sterilization of *E. coli*-Contaminated Needles

Two 20G needles were clipped, leaving 3 mm of the metal shaft attached to the plastic mounts. Tubes were constructed by cutting the ends off the plastic shaft of a 3 ml syringe and plugging each end with the rubber portions from two plungers. One ml of an overnight culture of *E. coli* was passed through each needle. Each needle was placed in a tube with 1 ml luria broth (LB) medium. There was approximately 0.2 ml of air left at the top of each tube.

One tube was subjected to 10 cycles of pressure treatment (each cycle including 30 seconds at 37,000 psi, followed by 30 seconds at 14.7 psi) at 22.2° C. The second tube was placed inside the pressure chamber for 10 minutes at 22.2° C. but was not subjected to pressure treatment.

After pressure treatment, the needles were removed from the tubes and 0.2 ml LB was passed through each needle. Half of the 0.2 ml LB was spread on an LB plate. The remaining 0.1 ml LB was diluted (1:10, 1:100, 1:1,000, ad 1:10,000) and spread on four LB plates. All plates were grown overnight at 37° C. Colonies were counted on each plate and the number of colony forming units (cfu) within each LB sample was calculated.

A dramatic difference was observed in the colony forming activity of the LB medium passed through the treated and untreated needles. There were 10 cfu in the 0.2 ml passed through the pressure treated needle, while there was $9.2 \times 10^5$ cfu present in the LB passed through the untreated needle, nearly a 100,000-fold difference.

Example 8
Pressure-Shock Sterilization

As a model for pathogenic viruses, fresh frozen plasma is spiked with 108 plaque forming units (pfu) per ml of lambda bacteriophage stabilized with 10% glucose and 4 mM sodium caprylate. The plasma is placed in a high pressure vessel containing 50% ethylene glycol as a pressure transmitting medium and the temperature is equilibrated to −10° C. The pressure is increased to 150,000 psi over a period of 1 second and held at that pressure for an additional 1 second. The pressure is then released over the course of 2 seconds. The plasma sample is removed and dilutions are plated on lawns of *E. coli*. The plasma sample is found to be substantially free of infectious virus. The plasma proteins are analyzed by various methods including HPLC, IgG antigen binding, fluorescence enhancement of dansyl sarcosine by HSA, and clotting assays to assess the integrity of the clotting factors.

Example 9
Pressure-Enhanced Photochemical Inactivation of Viruses

A sample of bovine serum is inoculated with $10^8$ plaque forming units (pfu) per ml of lambda bacteriophage. 0.15 mM of psoralen is added. The sample is split into three aliquots. The three samples are treated as follows:

(1) no further treatment
(2) pressurization to 30,000 psi
(3) pressurization to 30,000 psi and simultaneous exposure to UVA light for 10 minutes.

All samples are held at a temperature of 25° C. throughout the experiment. Treatment with pressure and light is accomplished by loading the sample into a quartz bottle with a polyethylene cap. The bottle is placed in an ethanol-filled high pressure spectroscopy cell (ISS, Champaign, Ill.) and pressurized. Samples are illuminated by aligning a window of the spectroscopy cell with a UVA lamp at a fixed distance. After treatment, the serum is serially diluted, mixed with *E. coli* and plated on agar. After overnight incubation at 37° C., the plaques on the plates are counted to arrive at the relative reduction of viral titer due to pressurization and the combination of pressurization and illumination. It is found that a significantly greater degree of viral inactivation is observed in sample #3, relative to samples #1 and #2. The experiment is repeated with lower concentrations of psoralen with the result that the combination of pressure and UVA light gives a rate of inactivation similar to that obtained by UVA alone, while resulting in less damage to therapeutic proteins. Similar experiments reveal that less light intensity or time of illumination is needed when the sample is pressurized. Experiments also show that nucleic-acid binding dyes that act in conjunction with oxygen (e.g. methylene blue) give results similar to those seen with psoralens.

Example 10
Pressure Enhanced Chemical Inactivation of Viruses

A sample of bovine serum is inoculated with $10^8$ plaque forming units (pfu) per ml of lambda bacteriophage. The sample is split into four aliquots. The samples are treated as follows:

1 no treatment
2 0.1 mM iodine added and incubated for 10 minutes
3 0.1 mM iodine added and pressurized to 30,000 psi for 10 minutes
4 pressure of 30,000 psi for 10 minutes All samples are held at a temperature of 25° C. throughout the experiment. After treatment, the reaction is quenched with a reducing agent and the serum is serially diluted, mixed with *E. coli* and plated on agar. After overnight incubation at 37° C., the plaques on the plates are counted to arrive at the relative reduction of viral titer due to pressurization and the combination of pressurization and chemical treatment. It is found that sample #3 has significantly greater reduction in viral titer (as compared to sample #1) than the sum of the reductions observed from samples #2 and #4, demonstrating a synergistic effect of pressure and iodine. Similar experiments are carried out with lower concentrations of chemical additives and it is found that pressure allows equivalent viral inactivation with lower concentrations of iodine or with shorter incubation time.

Example 11
Pressure Pulsation of Frozen Samples

A culture of *Saccharomyces cerevisiae* (baker's yeast) was grown overnight in YPD medium at 30° C. and the cell density was counted by light microscopy. The yeast were precipitated by centrifugation at 10,000 g for 1 min and washed with PBS. The supernatant was discarded and the pellet was resuspended in 270 pl of lysis buffer (2% Tritonx 100, 1% SDS, 100 mM Tris-HCL (pH 8), 1 mM EDTA). The yeast was stored at −20° C. until use. The yeast samples were placed in a pressurizing apparatus that was filled with ethylene glycol and regulated to −5° C. The pressure was raised to 2000 psi for 5 minutes and lowered to atmospheric pressure for 5 minutes. The sample was then briefly vortexed, and centrifuged at 10,000 g for 1 minute to remove the cell debris. The supernatant was collected and purified by extraction with phenol:chloroform:isoamyl alcohol and the DNA was quantified using the PicoGreen fluorescent dye (Molecular Probes, WA). The yield was compared to a control sample which was disrupted by vortexing with glass beads in lysis buffer (Rose, Winston and Hieter, "Methods in Yeast Genetics"). The sample which was pressurized to 2000 psi yielded 50% of the amount of DNA in the positive control, while the sample which was pressurized to 15,000 psi yielded DNA equal to only 10% of the control.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for sterilizing a material comprising at least one desired protein, the method comprising:
providing said material and, while maintaining the temperature of the material at 4° C. or lower, increasing the pressure to an elevated pressure sufficient to sterilize the material but insufficient to irreversibly denatured the desired protein, thereby providing a sterilized material.

2. The method of claim 1, wherein the initial pressure is about 1 atm.

3. The method of claim 1, wherein the initial temperature is between −40° C. and 0° C.

4. The method of claim 3, wherein the initial temperature is between −20° C. and −5° C.

5. The method of claim 1, wherein the elevated pressure is in the range of about 5,000 psi to about 50,000 psi.

6. The method of claim 1, further comprising repeatedly cycling the pressure between the elevated pressure and the initial pressure.

7. The method of claim 6, wherein the initial temperature is in the range from about −40° C. and 4° C.

8. The method of claim 1, further comprising cooling the material to a subzero temperature.

9. The method of claim 8, wherein the cooling step is carried out prior to the pressure increasing step.

10. The method of claim 1, wherein the material being sterilized is selected from the group consisting of a biological sample, blood plasma, serum, living tissue, medical or military equipment, a foodstuff, a pharmaceutical preparation, and a vaccine.

11. The method of claim 1, wherein the material being sterilized is initially contaminated with at least one of a bacterium, a virus, a fungus, a protist, a nucleic acid, and a protein.

12. The method of claim 1, wherein a protein stabilizing agent is added prior to sterilization.

13. The method of claim 12, wherein the protein stabilizing agent is selected from the group consisting of sugars, glycerol, a hydrophilic polymer, a cyclodextrin, a caprylate, acetyl tryptophanoate, polyethylene glycol, anti-oxidant, and a protein specific ligand.

14. The method of claim 1, wherein the material to be sterilized is provided in its final packaging, the packaging being adapted to transmit pressure without rupture.

15. The method of claim 14, wherein the packaging is hermetically sealed in flexible plastic.

16. The method of claim 14, wherein the packaging is a syringe and pressure is transmitted via a plunger.

17. A method for sterilizing a material comprising at least one desired protein, the method comprising:
providing said material and, while maintaining the temperature of the material below 25° C., increasing the pressure to an elevated pressure sufficient to sterlize the material but insufficient to irreversibly denature the desired protein, wherein the elevated pressure is in the range of about 10,000 to about 30,000 psi, thereby providing a sterilized material.

18. A method for sterilizing a material comprising at least one desired protein, the method comprising:
providing said material and, while maintaining the temperature of the material below 25° C., increasing the pressure to an elevated pressure sufficient to sterilize the material but insufficient to irreversibly denature to desired protein, and further comprising cooling the material to a subzero temperature after the pressure increasing step,
thereby providing a sterilized material.

19. A method for sterilizing a material comprising at least one desired protein, the method comprising:
providing said material and, while maintaining the temperature of the material below 25° C., increasing the pressure to an elevated pressure sufficient to sterilize the material but insufficient to irreversibly denature the desired protein, and further comprising cooling the material to a decreased temperature, wherein the decreased temperature is in the range from about −40° C. to about 4° C.
thereby providing a sterilized material.

20. The method of claim 19, wherein the decreased temperature is in the range from about −20 to about −5° C.

21. A method for sterilizing a material comprising at least one desired protein, the method comprising:
providing said material and, while maintaining the temperature of the material below 25° C., increasing the pressure to an elevated pressure sufficient to sterilize the material but insufficient to irreversibly denature the desired protein;
warming the material to the initial temperature, and then decreasing the pressure,
thereby providing a sterilized material.

22. A method for sterilizing a material comprising at least one desired protein, the method comprising:
providing said material and, while maintaining the temperature of the material below 25° C., increasing the pressure to an elevated pressure sufficient to sterilize the material but insufficient to irreversibly denature the desired protein;
decreasing the pressure; and then
warming the material to the initial temperature, thereby providing a sterilized material.

23. A method for sterilizing a material comprising at least one desired protein, the method comprising:
providing said material at an initial pressure and temperature;
cooling the material to decreased temperature below 25° C., then, while maintaining the temperature of the material at the decreased temperature,
increasing the pressure to an elevated pressure sufficient to sterilize the material but insufficient to irreversibly denature the desired protein, and
repeatedly cycling the pressure between the elevated pressure and the initial pressure,
thereby providing a sterilized material.

24. The method of claim 23, wherein said decreased temperature is in the range from about −40° C. to about 4° C.

25. The method of claim 23, wherein the decreased temperature is in the range from about −20° C. to about −5° C.

26. A method of producing a vaccine against a pathogen, the method comprising:

obtaining a suspension of pathogenic cells;

sterilizing the suspension by the method of claim 15; and adding an adjuvant to the sterilized suspension to produce a vaccine.

27. The method of claim 26, further comprising removing toxins from the suspension after the sterilizing step.

28. The method of claim 26, wherein the material to be sterilized is provided in its final packaging, the packaging being adapted to transmit pressure without rupture.

29. The method of claim 28, wherein the packaging is hermetically sealed in flexible plastic.

30. The method of claim 28, wherein the packaging is a syringe and a pressure is transmitted via a plunger.

31. A method for sterilizing a material, the method comprising:

providing a material at an initial pressure and temperature;

increasing the pressure to an elevated pressure insufficient to irreversibly denature proteins of interest; and decreasing the pressure to the initial pressure, thereby providing a sterilized material, wherein the material to be sterilized includes a phase-change catalyst.

32. A material sterilized by the method of claim 1.

33. A method for sterilizing a sample that includes at least one desired protein, the method comprising:

providing the sample at an initial pressure;

increasing the pressure to a pressure sufficient to inactivate pathogens;

maintaining the elevated pressure for a period of less than about 5 seconds; and restoring the initial pressure to provide a sterilized sample and to avoid substantial aggregation of the desired protein.

* * * * *